(12) United States Patent
Ma (10) Patent No.: US 8,022,157 B2
(45) Date of Patent: Sep. 20, 2011

(54) LIGHT SENSITIVE INITIATOR INTEGRATED POLYDIMETHYLSILOXANE

(75) Inventor: Hongwei Ma, Beijing (CN)

(73) Assignee: Peking University, Beijing (CN)

( * ) Notice: Subject to any disclaimer, the term of this patent is extended or adjusted under 35 U.S.C. 154(b) by 141 days.

(21) Appl. No.: 12/529,229

(22) PCT Filed: Aug. 29, 2008

(86) PCT No.: PCT/CN2008/072205
§ 371 (c)(1),
(2), (4) Date: Aug. 31, 2009

(87) PCT Pub. No.: WO2010/022564
PCT Pub. Date: Mar. 4, 2010

(65) Prior Publication Data
US 2011/0021730 A1 Jan. 27, 2011

(51) Int. Cl.
*C08F 230/08* (2006.01)
*C07C 205/59* (2006.01)
(52) U.S. Cl. .................. 526/279; 560/20
(58) Field of Classification Search .......... 526/279; 560/20
See application file for complete search history.

(56) References Cited

U.S. PATENT DOCUMENTS

| | | | |
|---|---|---|---|
| 4,153,641 | A | 5/1979 | Deichert et al. |
| 2007/0237947 | A1 | 10/2007 | Gleason et al. |

FOREIGN PATENT DOCUMENTS

| | | |
|---|---|---|
| CN | 1810912 A | 8/2006 |
| GB | 2082584 | 3/1982 |
| WO | WO 2004/090065 | 10/2004 |
| WO | WO 2004/108708 | 12/2004 |
| WO | WO 2005/084191 | 9/2005 |

OTHER PUBLICATIONS

Besson et al. "A Novel and Simplified Procedure for Patterning Hydrophobic and Hydrophilic SAMs for Microfluidic Devices by Using UV Photolithography" Langmuir 2006, 22, 8346-8352.*
International Search Report and Written Opinion issued in PCT/CN2008/072205, mailed Jun. 11, 2009.
El-Ali, Jamil et al., "Cells on chips," Nature, vol. 442, Jul. 27, 2006, pp. 403-411.
Elbert, D. L. et al., "Surface Treatments of Polymers for Biocompatibility," Annu. Rev. of Mater. Sci., vol. 26, 1996, pp. 365-394.
Gudipati, C. S. et al., "The Antifouling and Fouling-Release Performance of Hyperbranched Fluoropolymer (HBFP)-Poly(ethylene glycol) (PEG) Composite Coatings Evaluated by Adsorption of Biomacromolecules and the Green Fouling Alga *Ulva*," Langmuir; Am. Chem.Soc., vol. 21, No. 7, 2005, pp. 3044-3053.
Huang, Bo et al., "Counting Low-Copy Number Proteins in a Single Cell," Science, vol. 315, No. 5, Jan. 5, 2007, pp. 81-84.
Huang, Bo et al., "Use of a Mixture of *n*-Dodecyl-β-D-maltoside and Sodium Dodecyl Sulfate in Poly(dimethylsiloxane) Microchips to Suppress Adhesion and Promote Separation of Proteins," Anal. Chem., vol. 79, No. 23, pp. 9145-9149.

(Continued)

*Primary Examiner* — Robert Loewe
(74) *Attorney, Agent, or Firm* — Foley & Lardner LLP (57) ABSTRACT

Disclosed herein is a surface functionalized poly(dimethylsiloxane) (PDMS) and methods for making the same. The surface functionalized poly(dimethylsiloxane) (PDMS) disclosed herein is applicable in the general field of microfluidics, bioMEMS (bio-microelectromechanical systems), soft lithography and other related biotechnology fields.

19 Claims, 3 Drawing Sheets

OTHER PUBLICATIONS

Lee, Bong Soo et al., "Surface-Initiated, Atom Transfer Radical Polymerization of Oligo(ethylene glycol) Methyl Ether Methacrylate and Subsequent Click Chemistry for Bioconjugation," Biomacromolecules, vol. 8, No. 2, 2007, pp. 744-749.

Ma, Hongwei et al., "Applications of Surface Initiated Polymerization in Surface Modification of Biomaterials: an Ultra-low Initiator Density Strategy," Abstracts of the 26$^{th}$ Chinese Chemical Society Congress, Part 3: 07-O-022, Jul. 13-16, 2008.

Makamba, Honest et al., "Surface modification of poly(dimethylsiloxane) microchannels," Electrophoresis, vol. 24, No. 21, 2003, pp. 3607-3619.

Marmur, Abraham, "The Lotus Effect: Superhydrophobicity and Metastability," Langmuir, Am. Chem. Soc., 2004, pp. 3517-3519.

Psaltis, Demetri et al., "Developing optofluidic technology through the fusion of microfluidics and optics," Nature, vol. 442, Jul. 27, 2006, pp. 381-386.

Song, Helen et al., "On-Chip Titration of an Anticoagulant Argatroban and Determination of the Clotting Time Within Whole Blood or Plasma Using a Plug-Based Microfluidic System," Anal. Chem., vol. 78, No. 14, Jul. 15, 2006, pp. 4839-4849.

Toepke, M. W. et al., "PDMS absorption of small molecules and consequences in microfluidic applications," Lab Chip, vol. 6, The Royal Society of Chemistry, 2006, pp. 1484-1486.

Whitesides, George M. et al., "The origins and the future of microfluidics," Nature, vol. 442, Jul. 27, 2006, pp. 368-373.

Wu, Yuanzi et al., "A Facile Method for Permanent and Functional Surface Modification of Poly(dimethylsiloxane)," J. Am. Chem. Soc., vol. 129, No. 23, 2007, pp. 7226-7227.

Xia, Younan et al., "Soft Lithography," Angew. Chem. Int. Ed., vol. 37, 1998, pp. 550-575.

Xiao, Deqing et al., "Chemical Modification of the Surface of Poly(dimethylsiloxane) by Atom-Transfer Radical Polymerization of Acrylamide," Langmuir, vol. 18, No. 25, Am. Chem. Soc., 2002, pp. 9971-9976.

Zheng, Yongmei et al., "Directional adhesion of superhydrophobic butterfly wings," Soft Matter, vol. 3, The Royal Society of Chemistry, 2007, pp. 178-182.

* cited by examiner

LIGHT SENSITIVE INITIATOR INTEGRATED POLYDIMETHYLSILOXANE

CROSS-REFERENCE TO RELATED APPLICATIONS

The present application claims priority as a national stage application of International Application No. PCT/CN2008/072205 filed on Aug. 29, 2008, the entire contents of which are incorporated herein by reference in its entirety.

FIELD OF INVENTION

Disclosed herein is a surface functionalized poly(dimethylsiloxane) (PDMS) and methods for making the same. The surface functionalized poly(dimethylsiloxane) (PDMS) disclosed herein is applicable in the general field of microfluidics, bioMEMS (bio-microelectromechanical systems), soft lithography, and other related biotechnology fields.

BACKGROUND OF THE INVENTION

Poly(dimethylsiloxane) (PDMS) is the choice of material for a wide range of applications (Whitesides, G. M. Nature 2006, 442, 368-3731; Psaltis, D.; et al. Nature 2006, 442, 381-386; El-Ali, J.; et al. Nature 2006, 442, 403-411) due to its many advantageous properties. These properties include chemical inertness, non-toxicity, ease of handling, and commercial availability. Strategies for PDMS surface modification have been developed, such as physisorption and chemical coupling. Physisorption of materials to a PDMS surface, such as surfactants (Huang, B.; et al. Science 2007, 315, 81-84) and polyelectrolytes (Liu, Y.; et al. Anal. Chem. 2000, 72, 5939-5944) are driven by hydrophobic and electrostatic forces, respectively. Chemical coupling is stable but generally involves high-energy bombardment (i.e., plasma) to PDMS surface (Donzel, C.; et al. Adv. Mater. 2001, 13, 1164). A number of issues are associated with chemical coupling: (1) plasma treatment is easy, but not sustainable (Olah, A.; et al. Appl. Surf. Sci. 2005, 239, 410-423), (2) high-energy bombardment has the tendency to damage PDMS and is only applicable to planar surfaces because of its limited penetration depth, and (3) the concentration gradient in "grafting to" strategy prevents the preparation of thick and dense films (Ma, H.; et al. Adv. Funct. Mater. 2005, 16, 640-648).

SUMMARY OF THE INVENTION

An alternative to the development of new materials is modifying the surface of PDMS. However, a condition of such methods is that the surface modified PDMS would ideally retain the desired bulk properties of unmodified PDMS. Recently, Ma et al., reported a facile method for permanent and functional surface modification of PDMS based on a commercial material (Wu, Y.; et al. J. Am. Chem. Soc. 2007, 129, 7226-7227). Further study of surface initiated polymerization from iPDMS confirmed that permanent and functional surface coating was successfully immobilized. However, this method does not provide a way to selectively (spatially) modify/functionalize the surface of iPDMS, which is the key for iPDMS to be useful in many applications in the field of microfluidics, bioMEMS, soft lithography and other related biotechnology fields. Disclosed herein is a surface functionalized poly(dimethylsiloxane) (PDMS) and methods for making the same. The surface functionalized poly(dimethylsiloxane) (PDMS) disclosed herein is applicable in the general field of microfluidics, bioMEMS (bio-microelectromechanical systems), soft lithography and other related biotechnology fields.

Disclosed herein is a compound of Formula I:

I wherein:
$R^1$ is hydrogen or methyl;
$R^2$ is selected from the group consisting of alkyl optionally substituted with 1-3 $R^4$ groups, haloalkyl optionally substituted with 1-3 $R^4$ groups, aryl optionally substituted with 1-4 $R^4$ groups, cycloalkyl optionally substituted with 1-4 $R^4$ groups, heterocycloalkyl optionally substituted with 1-4 $R^4$ groups, and heteroaryl optionally substituted with 1-4 $R^4$ groups;
X is selected from the group consisting of nitro, $-N(R^3)_3^+$, trifluoromethyl, cyano, $-C(O)OR^3$, $-C(O)R^3$, where $R^3$ is hydrogen or alkyl; and
$L^1$ and $L^2$ are independently selected from the group consisting of a direct bond, methylene optionally substituted with 1-2 $R^4$ groups, $(C_2-C_{12})$alkylene optionally substituted with 1-4 $R^4$ groups, $(C_6-C_{12})$arylene optionally substituted with 1-4 $R^4$ groups, $(C_3-C_{12})$cycloalkylene optionally substituted with 1-4 $R^4$ groups, $(C_3-C_{12})$heterocycloalkylene optionally substituted with 1-4 $R^4$ groups, and $(C_6-C_{12})$heteroarylene optionally substituted with 1-4 $R^4$ groups; and
$R^4$ is selected from the group consisting of halo, nitro, cyano, oxo, aminoacyl, aminoacyloxy, carboxyl, carboxyl ester, carbonate ester, aminosulfonyl, $(C_1-C_{10})$alkyl, $(C_1-C_{10})$haloalkyl, $(C_1-C_{10})$alkoxy, $(C_6-C_{12})$aryl, $(C_5-C_{12})$heteroaryl, $(C_6-C_{12})$aryloxy, $(C_3-C_{12})$cycloalkyl and $(C_3-C_{12})$heterocycloalkyl.

In one embodiment, the compound is of Formula II.

II

Also disclosed herein is a surface functionalized poly(dimethylsiloxane) (PDMS), comprising a polydimethyl siloxane (PDMS) substrate having a compound of Formula III incorporated therein:

wherein:

$R^1$ is hydrogen or methyl;

$R^2$ is selected from the group consisting of alkyl optionally substituted with 1-3 $R^4$ groups, haloalkyl optionally substituted with 1-3 $R^4$ groups, aryl optionally substituted with 1-4 $R^4$ groups, cycloalkyl optionally substituted with 1-4 $R^4$ groups, heterocycloalkyl optionally substituted with 1-4 $R^4$ groups, and heteroaryl optionally substituted with 1-4 $R^4$ groups;

X is selected from the group consisting of nitro, $-N(R^3)_3^+$, trifluoromethyl, cyano, $-C(O)OR^3$, $-C(O)R^3$, where $R^3$ is hydrogen or alkyl; and $L^1$ and $L^2$ are independently selected from the group consisting of a direct bond, methylene optionally substituted with 1-2 $R^4$ groups, $(C_2\text{-}C_{12})$alkylene optionally substituted with 1-4 $R^4$ groups, $(C_6\text{-}C_{12})$arylene optionally substituted with 1-4 $R^4$ groups, $(C_3\text{-}C_{12})$cycloalkylene optionally substituted with 1-4 $R^4$ groups, $(C_3\text{-}C_{12})$heterocycloalkylene optionally substituted with 1-4 $R^4$ groups, and $(C_6\text{-}C_{12})$heteroarylene optionally substituted with 1-4 $R^4$ groups; and $R^4$ is selected from the group consisting of halo, nitro, cyano, oxo, aminoacyl, aminoacyloxy, carboxyl, carboxyl ester, carbonate ester, aminosulfonyl, $(C_1\text{-}C_{10})$alkyl, $(C_1\text{-}C_{10})$haloalkyl, $(C_1\text{-}C_{10})$alkoxy, $(C_6\text{-}C_{12})$aryl, $(C_5\text{-}C_{12})$heteroaryl, $(C_6\text{-}C_{12})$aryloxy, $(C_3\text{-}C_{12})$cycloalkyl and $(C_3\text{-}C_{12})$heterocycloalkyl.

In some embodiments, the surface functionalized poly(dimethylsiloxane) (PDMS) has the compound incorporated therein at a ratio of from about 11:0.5 to about 11:10⁻³. The concentration of the compound can be varied depending on the application, provided that the surface functionalized poly(dimethylsiloxane) (PDMS) possesses similar physical properties to that of unfunctionalized poly(dimethylsiloxane) (PDMS). In one embodiment, the contact angle is from about 0 to about 155 degrees.

Disclosed herein is a method of preparing a surface functionalized poly(dimethylsiloxane) (PDMS) substrate, comprising contacting a monomer mixture with a compound of Formula I under polymerization conditions:

wherein:

$R^1$ is hydrogen or methyl;

$R^2$ is selected from the group consisting of alkyl optionally substituted with 1-3 $R^4$ groups, haloalkyl optionally substituted with 1-3 $R^4$ groups, aryl optionally substituted with 1-4 $R^4$ groups, cycloalkyl optionally substituted with 1-4 $R^4$ groups, heterocycloalkyl optionally substituted with 1-4 $R^4$ groups, and heteroaryl optionally substituted with 1-4 $R^4$ groups;

X is selected from the group consisting of nitro, $-N(R^3)_3^+$, trifluoromethyl, cyano, $-C(O)OR^3$, $-C(O)R^3$, where $R^3$ is hydrogen or alkyl; and $L^1$ and $L^2$ are independently selected from the group consisting of a direct bond, methylene optionally substituted with 1-2 $R^4$ groups, $(C_2\text{-}C_{12})$alkylene optionally substituted with 1-4 $R^4$ groups, $(C_6\text{-}C_{12})$arylene optionally substituted with 1-4 $R^4$ groups, $(C_3\text{-}C_{12})$cycloalkylene optionally substituted with 1-4 $R^4$ groups, $(C_3\text{-}C_{12})$heterocycloalkylene optionally substituted with 1-4 $R^4$ groups, and $(C_6\text{-}C_{12})$heteroarylene optionally substituted with 1-4 $R^4$ groups; and $R^4$ is selected from the group consisting of halo, nitro, cyano, oxo, aminoacyl, aminoacyloxy, carboxyl, carboxyl ester, carbonate ester, aminosulfonyl, $(C_1\text{-}C_{10})$alkyl, $(C_1\text{-}C_{10})$haloalkyl, $(C_1\text{-}C_{10})$alkoxy, $(C_6\text{-}C_{12})$aryl, $(C_5\text{-}C_{12})$heteroaryl, $(C_6\text{-}C_{12})$aryloxy, $(C_3\text{-}C_{12})$cycloalkyl and $(C_3\text{-}C_{12})$heterocycloalkyl;

to provide a functionalized poly(dimethylsiloxane) (PDMS) substrate.

Also disclosed herein is a method of preparing a surface functionalized poly(dimethylsiloxane) (PDMS) substrate, comprising contacting a monomer mixture with a compound of Formula II under polymerization conditions.

In some embodiments, the surface functionalized poly(dimethylsiloxane) (PDMS) further comprises at least one indentation on the surface. This can be accomplished using a number of known methods, such as standard soft lithography or with the use of a mold. It is contemplated that the surface functionalized poly(dimethylsiloxane) (PDMS) can be produced in any theoretical size or shape so long as the bulk properties of the poly(dimethylsiloxane) (PDMS) are not substantially effected. In one embodiment, the surface functionalized poly(dimethylsiloxane) (PDMS) is a microfluidic device.

Disclosed herein is a method for producing a microfluidic device, comprising:

1) providing a poly(dimethylsiloxane) (PDMS) polymer substrate having a compound of Formula III incorporated therein:

wherein:

R[1] is hydrogen or methyl;

R[2] is selected from the group consisting of alkyl optionally substituted with 1-3 R[4] groups, haloalkyl optionally substituted with 1-3 R[4] groups, aryl optionally substituted with 1-4 R[4] groups, cycloalkyl optionally substituted with 1-4 R[4] groups, heterocycloalkyl optionally substituted with 1-4 R[4] groups, and heteroaryl optionally substituted with 1-4 R[4] groups;

X is selected from the group consisting of nitro, $-N(R^3)_3^+$, trifluoromethyl, cyano, $-C(O)OR^3$, $-C(O)R^3$, where R[3] is hydrogen or alkyl; and L[1] and L[2] are independently selected from the group consisting of a direct bond, methylene optionally substituted with 1-2 R[4] groups, $(C_2-C_{12})$alkylene optionally substituted with 1-4 R[4] groups, $(C_6-C_{12})$arylene optionally substituted with 1-4 R[4] groups, $(C_3-C_{12})$cycloalkylene optionally substituted with 1-4 R[4] groups, $(C_3-C_{12})$heterocycloalkylene optionally substituted with 1-4 R[4] groups, and $(C_6-C_{12})$heteroarylene optionally substituted with 1-4 R[4] groups; and R[4] is selected from the group consisting of halo, nitro, cyano, oxo, aminoacyl, aminoacyloxy, carboxyl, carboxyl ester, carbonate ester, aminosulfonyl, $(C_1-C_{10})$alkyl, $(C_1-C_{10})$haloalkyl, $(C_1-C_{10})$alkoxy, $(C_6-C_{12})$aryl, $(C_5-C_{12})$heteroaryl, $(C_6-C_{12})$aryloxy, $(C_3-C_{12})$cycloalkyl and $(C_3-C_{12})$heterocycloalkyl; and 2) applying a photomask to a surface of the functionalized poly(dimethylsiloxane) (PDMS) substrate; and 3) irradiating at a wavelength of from about 150 nm to about 400 nm, to produce the microfluidic device.

It is contemplated that the surface functionalized poly(dimethylsiloxane) (PDMS) disclosed herein can be used in all of the applications where standard PDMS is used. For example, these include but are not limited to, the fabrication of microfluidic devices, bioMEMS, microelectronics, biotechnology, microreactors, microsensors, microanalyzers, microoptics, and in research.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION OF THE INVENTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

ABBREVIATIONS AND DEFINITIONS

Unless otherwise stated all temperatures are in degrees Celsius (° C.). Also, in these examples and elsewhere, abbreviations have the following meanings:

TABLE 1

| Abbreviation | Term |
|---|---|
| MPa | megaPascal |
| PDMS | polydimethyl siloxane |
| M | molar |
| mg | milligram |
| mmol | millimole |
| mL | milliliter |
| ppm | parts per million |
| TMS | trimethylsilane |
| δ | chemical shift |
| NMR | nuclear magnetic resonance |
| v/v | volume/volume |
| N | normal |
| UV | Ultraviolet |
| HMPA | hexamethylphosphoramide |
| XPS | x-ray photoelectron spectroscopy |
| DMAP | 4-dimethylaminopyridine |
| DCC | dicyclohexylcarbodiimide |
| eV | electron volts |
| nm | nanometer |
| bioMEMS | biomicroelectromechanical systems |

As used herein, certain terms may have the following defined meanings.

As used herein, the term "comprising" means that the compositions and methods include the recited elements, but do not exclude others. "Consisting essentially of" when used to define compositions and methods, shall mean excluding other elements of any essential significance to the combination when used for the intended purpose. Thus, a composition consisting essentially of the elements as defined herein would not exclude trace contaminants or inert carriers. "Consisting of" shall mean excluding more than trace elements of other ingredients and substantial method steps for preparing the microfluidic device. Embodiments defined by each of these transition terms are within the scope of the present technology.

As used herein, the term "polydimethyl siloxane (PDMS) substrate" refers to a solid polydimethyl siloxane (PDMS)

polymer composed of at least one dimethylsiloxane monomer. In some instances, at least two dimethylsiloxane monomers are used to make the polydimethyl siloxane (PDMS) substrate. In some cases, monomers comprise a poly(dimethylsiloxane) having a sufficient number of vinyl groups and a silicon hydride containing monomer having a sufficient number of Si—H groups, such that the silicon hydride containing monomer forms more than one covalent bond with at least one vinyl group on the poly(dimethylsiloxane) and the resulting polymer substrate has a density of about 1 g mL$^{-1}$. The monomer mixtures may comprise additional components, such as other monomers or a catalyst, such as platinum. Various monomer mixtures are commercially available and include, for example, Sylgard® 184 (Dow Corning Corporation, Midland, Mich., United States), RTV 615 (Sil-Mid limited, Coleshill, West Midlands, United Kingdom) and ELASTOSiL® RT 601 (Wacker Chemie AG, San Jose, Calif., United States). The size of the polymer substrate is easily determined by one of skill in the art. It is contemplated that the size of the polymer substrate is not limited by any of the physical characteristics of the polymer. In addition, the shape of the polymer substrate can be dictated by the use of a mold. Such molds are well known to those of skill in the art.

The term "prepolymer" refers to a reactive low-molecular-weight macromolecule or an oligomer, capable of further polymerization. Examples of prepolymers include, but are not limited to, e.g., poly(dimethyl-methylvinylsiloxane) prepolymer and poly(dimethyl-methylhydrogensiloxane) precursors. The term "poly(dimethyl-methylhydrogensiloxane) precursors" refers to a reactive low-molecular-weight macromolecule or an oligomer of dimethylmethylhydrogensiloxane, capable of further polymerization. Polymerization of these prepolymers or monomers can be accomplished by, as an example, free radical polymerization, metal catalyzed polymerization, heat, or combination thereof. In some embodiments, polymerization is accomplished using both metal catalyzed polymerization and heat.

The term "monomer" has the meaning understood by those skilled in the chemical art. That is, a monomer is a chemical compound that is capable of forming a macromolecule of repeating units of itself, i.e., a polymer. The term "monomer" is also intended to include "oligomers" which consists of more than one monomer unit, capable of further polymerization. A "monomer mixture" refers to a mixture of two or more different monomers capable of being polymerized under polymerization conditions. In some embodiments, the monomer mixture comprises poly(dimethyl-methylvinylsiloxane) prepolymer and poly(dimethyl-methylhydrogensiloxane) precursors.

As used herein, the term "contact angle" refers to the angle at which a liquid interface meets a solid surface. On many hydrophilic surfaces, water droplets will exhibit contact angles of 0 degrees to 30 degrees. If the solid surface is hydrophobic, the contact angle will be larger than 90 degrees. In some embodiments, the contact angle of the surface functionalized poly(dimethylsiloxane) (PDMS) is from about 0 to about 155 degrees. In one embodiment the contact angle is from about 10 to about 145 degrees, or alternatively, from about 20 to about 135 degrees, or alternatively, from about 30 to about 135 degrees, or alternatively, from about 50 to about 135 degrees, or alternatively, from about 60 to about 135 degrees, or alternatively, from about 70 to about 135 degrees, or alternatively, from about 80 to about 135 degrees, or alternatively, from about 90 to about 120 degrees, or alternatively, from about 100 to about 120 degrees. In one embodiment, the contact angle is about 114 degrees.

The term "bonded" refers to a chemical bond. Various types of chemical bonds can be employed in the methods disclosed herein, either alone or in combination. Examples of bonds include a covalent bond, a polar covalent bond, an ionic bond and a hydrogen bond.

The term "reaction conditions" refers to conditions which comprise solvent (if required), time, temperature, pressure, concentration, and the like. It is well known to those skilled in the art that the reaction conditions may vary depending on the components which are being reacted.

The term "indentation" refers to a concave depression or cut on a surface. The indentations as disclosed herein can be of any possible shape, size or design. In some embodiments, the indentation is a microfluidic channel. In one embodiment, the indentation is a well. The indentations can be provided using a number of known methods, such as photolithography, soft lithography, isotropic or anisotropic etching, or with the use of a mold. Such technologies are well known in the art (Xia, et al., *Angew. Chem. Int. Ed*, 1998, 37, 550-575).

As used herein, the term "alkyl" refers to saturated monovalent hydrocarbyl groups having from 1 to 10 carbon atoms. This term is exemplified by groups such as methyl, ethyl, n-propyl, iso-propyl, n-butyl, t-butyl, n-pentyl, and the like.

As used herein, the term "alkenyl" refers to an hydrocarbyl group preferably having from 2 to 8 carbon atoms and having from 1 to 2 sites of alkenyl unsaturation. The term "terminal alkenyl" refers to an alkenyl group wherein a site of alkenyl unsaturation is at the end of the carbon chain.

As used herein, the term "haloalkyl" refers to an alkyl group as defined herein above, wherein one or more hydrogen has been replaced with a halo group. This term is exemplified by groups such as bromomethyl, trifluoromethyl, and the like.

As used herein, the term "cycloalkyl" refers to a saturated or an unsaturated but nonaromatic cyclic alkyl groups of from 3 to 10 carbon atoms having single or multiple cyclic rings including, by way of example, adamantyl, cyclopropyl, cyclobutyl, cyclopentyl, cyclooctyl, cyclohexenyl, and the like.

As used herein, the term "aryl" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2 benzoxazolinone, 2H-1,4-benzoxazin-3(4H)-one-7-yl, and the like) provided that the point of attachment is the aryl group.

As used herein, the term "heterocycloalkyl" and "heterocyclic" refers to a saturated or unsaturated (but not aromatic) group having a single ring or multiple condensed rings, from 1 to 10 carbon atoms, and from 1 to 4 hetero atoms selected from the group consisting of nitrogen, sulfur or oxygen within the ring wherein, in fused ring systems, one or more of the rings can be aryl or heteroaryl provided that the point of attachment is at the heterocycle.

As used herein, the term "heteroaryl" refers to an aromatic ring of from 1 to 15 carbon atoms, preferably from 1 to 10 carbon atoms, and 1 to 4 heteroatoms within the ring selected from the group consisting of oxygen, nitrogen, and sulfur. Such heteroaryl groups can have a single ring (e.g., pyridinyl, furyl, triazole or thienyl) or multiple condensed rings (e.g., indolizinyl or benzothienyl) provided the point of attachment is through a ring containing the heteroatom and that ring is aromatic. The nitrogen and/or sulfur ring atoms can optionally be oxidized to provide for the N-oxide or the sulfoxide, and sulfone derivatives. Examples of heteroaryls include but are not limited to, pyridinyl, pyrrolyl, indolyl, thiophenyl, thienyl, triazole, tetrazole, and furyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), triazole, tetrazole, piperidinyl, pyrrolidine, tetrahydrofuranyl, and the like.

As used herein, the term "alkylene" refers to divalent saturated aliphatic hydrocarbyl groups preferably having from 1 to 5 and more preferably 1 to 3 carbon atoms which are either straight-chained or branched. This term is exemplified by groups such as methylene (—CH$_2$—), ethylene (—CH$_2$CH$_2$—), n-propylene (—CH$_2$CH$_2$CH$_2$—), iso-propylene (—CH$_2$CH(CH$_3$)—) and the like. "(C$_{u-v}$)alkylene" refers to alkylene groups having from u to v carbon atoms. The alkylidene or alkylene groups include branched and straight chain hydrocarbyl groups. For example "(C$_{1-6}$)alkylene" is meant to include methylene, ethylene, propylene, 2-methylpropylene, pentylene, and the like.

As used herein, the term "arylene" refers to divalent aryl groups as defined above.

As used herein, the term "cycloalkylene" refers to divalent cycloalkyl groups as defined above.

As used herein, the term "heterocycloalkylene" refers to divalent heterocycloalkyl groups as defined above.

As used herein, the term "heteroarylene" refers to divalent heteroaryl groups as defined above.

As used herein, the term "halo" or "halogen" refers to fluoro, chloro, bromo, and iodo.

As used herein, the term "nitro" refers to the group —NO$_2$.

As used herein, the term "cyano" refers to the group —CN.

As used herein, the term "hydroxyl" refers to the group —OH.

As used herein, the term "amino" refers to the group —NH$_2$.

As used herein, the term "thio" refers to the group —SH.

As used herein, the term "oxo" refers to the atom (=O) or (—O$^-$).

As used herein, the term "aminoacyl" refers to the group —C(=O)NRR where each R is independently selected from the group consisting of hydrogen, alkyl, aryl, cycloalkyl, heteroaryl, and heterocycloalkyl, and where R$^{23}$ and R$^{24}$ are optionally joined together with the nitrogen bound thereto to form a heterocyclic group, and wherein alkyl, cycloalkyl, aryl, heteroaryl, and heterocycloalkyl, are as defined herein.

As used herein, the term "aminoacyloxy" refers to the group —O—C(=O)NRR where each R is independently selected from the group consisting of hydrogen, alkyl, aryl, cycloalkyl, heteroaryl, and heterocycloalkyl, and where R$^{23}$ and R$^{24}$ are optionally joined together with the nitrogen bound thereto to form a heterocyclic group, and wherein alkyl, cycloalkyl, aryl, heteroaryl, and heterocycloalkyl, are as defined herein.

The term "amido" refers to the groups —C(=O)—NR-alkyl, —C(=O)—NR-cycloalkyl, —C(=O)—NR-aryl, —C(=O)—NR-heteroaryl, —C(=O)—NR-heterocyclic, wherein R is hydrogen or alkyl.

The term "alpha-haloester" refers to the group —O—C(=O)-haloalkyl, wherein at least one halogen is at the alpha-position.

As used herein, the term "carboxyl" refers to —COOH or salts thereof.

As used herein, the term "carboxyl ester" refers to the groups —C(=O)—O-alkyl, —C(=O)—O-cycloalkyl, —C(=O)—O-aryl, —C(=O)—O-heteroaryl, —C(=O)—O-heterocyclic.

As used herein, the term "carbonate ester" refers to the groups —O—C(=O)—O-alkyl, —O—C(=O)—O-cycloalkyl, —O—C(=O)—O-aryl, —O—C(=O)—O-heteroaryl, —O—C(=O)—O-heterocyclic.

As used herein, the term "aminosulfonyl" refers to the group SO$_2$NRR wherein each R is independently selected from the group consisting of hydrogen, alkyl, aryl, cycloalkyl, heteroaryl, and heterocycloalkyl, and where R$^{23}$ and R$^{24}$ are optionally joined together with the nitrogen bound thereto to form a heterocyclic group, and wherein alkyl, cycloalkyl, aryl, heteroaryl, and heterocycloalkyl, are as defined herein.

As used herein, the term "alkoxy" refers to the group "alkyl-O—" which includes, by way of example, methoxy, ethoxy, n-propoxy, iso-propoxy, n-butoxy, t-butoxy, sec-butoxy, n-pentoxy, and the like.

As used herein, the term "aryloxy" refers to the group aryl-O— that includes, by way of example, phenoxy, naphthoxy, and the like.

Compounds

Disclosed herein is a compound of Formula I:

wherein:

R$^1$ is hydrogen or methyl;

R$^2$ is selected from the group consisting of alkyl optionally substituted with 1-3 R$^4$ groups, haloalkyl optionally substituted with 1-3 R$^4$ groups, aryl optionally substituted with 1-4 R$^4$ groups, cycloalkyl optionally substituted with 1-4 R$^4$ groups, heterocycloalkyl optionally substituted with 1-4 R$^4$ groups, and heteroaryl optionally substituted with 1-4 R$^4$ groups;

X is selected from the group consisting of nitro, —N(R$^3$)$_3$$^+$, trifluoromethyl, cyano, —C(O)OR$^3$, —C(O)R$^3$, where R$^3$ is hydrogen or alkyl; and L$^1$ and L$^2$ are independently selected from the group consisting of a direct bond, methylene optionally substituted with 1-2 R$^4$ groups, (C$_2$-C$_{12}$)alkylene optionally substituted with 1-4 R$^4$ groups, (C$_6$-C$_{12}$)arylene optionally substituted with 1-4 R$^4$ groups, (C$_3$-C$_{12}$)cycloalkylene optionally substituted with 1-4 R$^4$ groups, (C$_3$-C$_{12}$)heterocycloalkylene optionally substituted with 1-4 R$^4$ groups, and (C$_6$-C$_{12}$)heteroarylene optionally substituted with 1-4 R$^4$ groups; and R$^4$ is selected from the group consisting of halo, nitro, cyano, oxo, aminoacyl, aminoacyloxy, carboxyl, carboxyl ester, carbonate ester, aminosulfonyl, (C$_1$-C$_{10}$)alkyl, (C$_1$-

$C_{10}$)haloalkyl, ($C_1$-$C_{10}$)alkoxy, ($C_6$-$C_{12}$)aryl, ($C_5$-$C_{12}$)heteroaryl, ($C_6$-$C_{12}$)aryloxy, ($C_3$-$C_{12}$)cycloalkyl and ($C_3$-$C_{12}$)heterocycloalkyl.

In one embodiment, $R^1$ is hydrogen.

In one embodiment, $R^2$ is alkyl substituted with an oxo and halo group.

In one embodiment, X is nitro.

In one embodiment, $L^1$ and $L^2$ are ($C_1$-$C_{12}$)alkylene.

In one embodiment, $R^1$ is hydrogen; $R^2$ is alkyl substituted with an oxo and halo group; X is nitro; and $L^1$ and $L^2$ are ($C_1$-$C_{12}$)alkylene.

Also disclosed herein is a compound of Formula II.

II

Synthesis of the Compounds

The compounds described herein can be prepared from readily available starting materials using, for example, the following general methods, and procedures. It will be appreciated that where reaction conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) Protecting Groups in Organic Synthesis, 3rd Edition, Wiley, New York, and references cited therein.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

The compounds disclosed herein can be prepared by, but are not limited to, the synthetic protocols illustrated in Scheme 1. In Scheme 1, the substituents X, $R^1$, $R^2$, $R^{10}$, $L^1$ and $L^2$ are as defined herein.

Scheme 1

Compounds of Formula I can be prepared from compounds Ic and Id, wherein $R^{10}$ is a leaving group such as a mesylate or halogen. Compounds Ic and Id are reacted under standard substitution reaction conditions to provide Formula I. In some embodiments, additional reagents may be required to enhance the reactivity of certain starting materials, such as coupling agents like dicyclohexylcarbodiimide (DCC), and the like. Such reagents are commonly known to those of skill in the art and are generally acids, bases, oxidizing agents, reducing agents, or a solvent such as a polar solvent.

Compound Ic can be prepared from reacting compounds Ia and Ib under standard coupling conditions. Compound Ia is first activated with at least a stoichiometric amount and preferably a slight excess thereof of a coupling agent, such as a carbodiimide, in the presence of a base, such as dimethylaminopyridine.

Compounds Ib and Id can either be purchased from commercial sources or synthesized using methods known to those skilled in the art.

Surface Functionalized Poly(dimethylsiloxane) (PDMS)

Disclosed herein is a surface functionalized poly(dimethylsiloxane) (PDMS), comprising a polydimethyl siloxane (PDMS) substrate having a compound of Formula III incorporated therein:

wherein:

R¹ is hydrogen or methyl;

R² is selected from the group consisting of alkyl optionally substituted with 1-3 R⁴ groups, haloalkyl optionally substituted with 1-3 R⁴ groups, aryl optionally substituted with 1-4 R⁴ groups, cycloalkyl optionally substituted with 1-4 R⁴ groups, heterocycloalkyl optionally substituted with 1-4 R⁴ groups, and heteroaryl optionally substituted with 1-4 R⁴ groups;

X is selected from the group consisting of nitro, $-N(R^3)_3^+$, trifluoromethyl, cyano, $-C(O)OR^3$, $-C(O)R^3$, where $R^3$ is hydrogen or alkyl; and L¹ and L² are independently selected from the group consisting of a direct bond, methylene optionally substituted with 1-2 R⁴ groups, $(C_2-C_{12})$alkylene optionally substituted with 1-4 R⁴ groups, $(C_6-C_{12})$arylene optionally substituted with 1-4 R⁴ groups, $(C_3-C_{12})$cycloalkylene optionally substituted with 1-4 R⁴ groups, $(C_3-C_{12})$heterocycloalkylene optionally substituted with 1-4 R⁴ groups, and $(C_6-C_{12})$heteroarylene optionally substituted with 1-4 R⁴ groups; and R⁴ is selected from the group consisting of halo, nitro, cyano, oxo, aminoacyl, aminoacyloxy, carboxyl, carboxyl ester, carbonate ester, aminosulfonyl, $(C_1-C_{10})$alkyl, $(C_1-C_{10})$haloalkyl, $(C_1-C_{10})$alkoxy, $(C_6-C_{12})$aryl, $(C_5-C_{12})$heteroaryl, $(C_6-C_{12})$aryloxy, $(C_3-C_{12})$cycloalkyl and $(C_3-C_{12})$heterocycloalkyl.

In one embodiment, R¹ is hydrogen.

In one embodiment, R² is alkyl substituted with an oxo and halo group.

In one embodiment, X is nitro.

In one embodiment, L¹ and L² are $(C_1-C_{12})$alkylene.

In one embodiment, R¹ is hydrogen; R² is alkyl substituted with an oxo and halo group; X is nitro; and L¹ and L² are $(C_1-C_{12})$alkylene.

Also disclosed herein is a surface functionalized poly(dimethylsiloxane) (PDMS), comprising a polydimethyl siloxane (PDMS) substrate having a compound of Formula IV incorporated therein:

In one embodiment, the surface functionalized poly(dimethylsiloxane) (PDMS) has the compound incorporated therein at a ratio of from about 11:0.5 to about $11:10^{-3}$. The concentration of initiator can be varied depending on the application, provided that the surface functionalized poly (dimethylsiloxane) (PDMS) possesses similar physical properties to that of unfunctionalized poly(dimethylsiloxane) (PDMS). In one embodiment, the contact angle of unfunctionalized poly(dimethylsiloxane) (PDMS) is from about 0 to about 155 degrees. In one embodiment the contact angle is from about 0 to about 149 degrees, or alternatively, from about 10 to about 145 degrees, or alternatively, from about 20 to about 135 degrees, or alternatively, from about 30 to about 135 degrees, or alternatively, from about 50 to about 135 degrees, or alternatively, from about 60 to about 135 degrees, or alternatively, from about 70 to about 135 degrees, or alternatively, from about 80 to about 135 degrees, or alternatively, from about 90 to about 120 degrees, or alternatively, from about 100 to about 120 degrees. In one embodiment, the contact angle is about 114 degrees.

Figure 1:
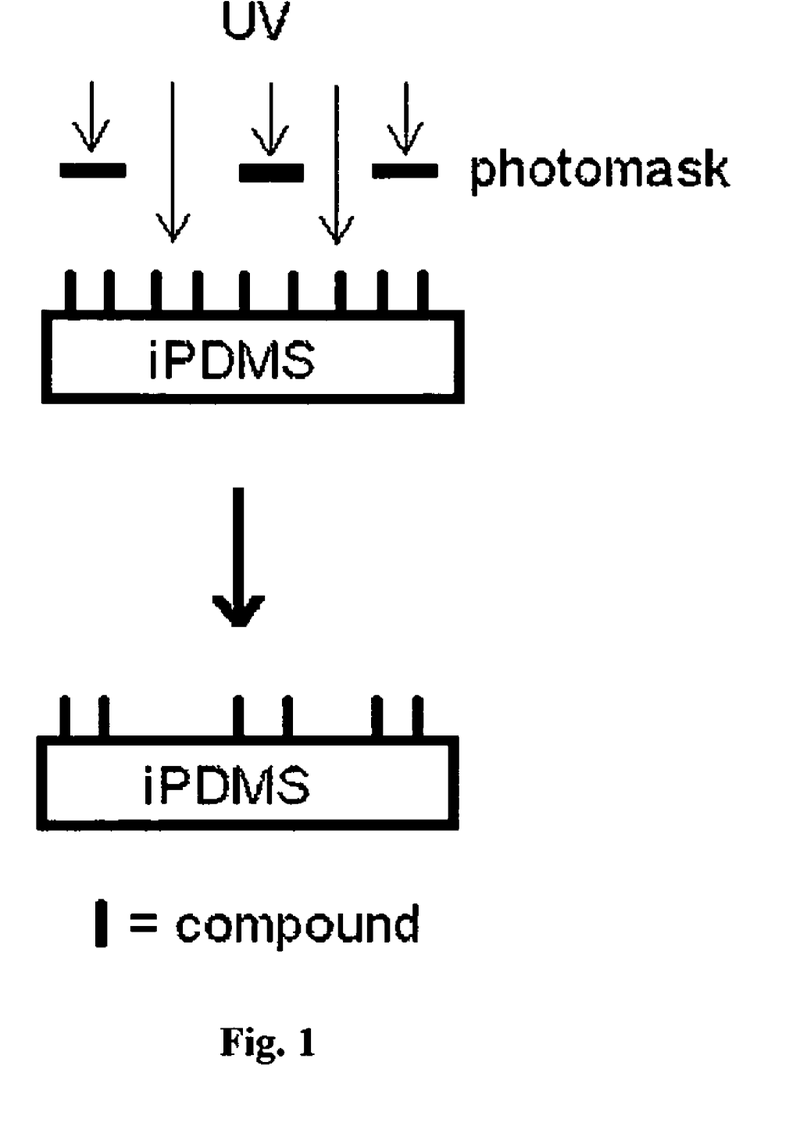
FIG. 1 is a schematic of an illustrative embodiment of the formation of a pattern on the surface of the surface functionalized PDMS via photolithography.

The surface functionalized poly(dimethylsiloxane) (PDMS) can be patterned using irradiation with UV light with a photomask, as is depicted in FIG. 1.

Methods of Preparing a Surface Functionalized Poly(dimethylsiloxane) (PDMS)

Disclosed herein is a method of preparing a surface functionalized poly(dimethylsiloxane) (PDMS) substrate, comprising contacting a monomer mixture with a compound of Formula I under polymerization conditions:

wherein:

R¹ is hydrogen or methyl;

R² is selected from the group consisting of alkyl optionally substituted with 1-3 R⁴ groups, haloalkyl optionally substituted with 1-3 R⁴ groups, aryl optionally substituted with 1-4 R⁴ groups, cycloalkyl optionally substituted with 1-4 R⁴ groups, heterocycloalkyl optionally substituted with 1-4 R⁴ groups, and heteroaryl optionally substituted with 1-4 R⁴ groups;

X is selected from the group consisting of nitro, $-N(R^3)_3^+$, trifluoromethyl, cyano, $-C(O)OR^3$, $-C(O)R^3$, where $R^3$ is hydrogen or alkyl; and L¹ and L² are independently selected from the group consisting of a direct bond, methylene optionally substituted with 1-2 R⁴ groups, $(C_2-C_{12})$alkylene optionally substituted with 1-4 R⁴ groups, $(C_6-C_{12})$arylene optionally substituted with 1-4 R⁴ groups, $(C_3-C_{12})$cycloalkylene optionally substituted with 1-4 R⁴ groups, $(C_3-C_{12})$heterocycloalkylene optionally substituted with 1-4 R⁴ groups, and $(C_6-C_{12})$heteroarylene optionally substituted with 1-4 R⁴ groups; and R⁴ is selected from the group consisting of halo, nitro, cyano, oxo, aminoacyl, aminoacyloxy, carboxyl, carboxyl ester, carbonate ester, aminosulfonyl, $(C_1$-$C_{10})$alkyl, $(C_1$-$C_{10})$haloalkyl, $(C_1$-$C_{10})$alkoxy, $(C_6$-$C_{12})$aryl, $(C_5$-$C_{12})$heteroaryl, $(C_6$-$C_{12})$aryloxy, $(C_3$-$C_{12})$cycloalkyl and $(C_3$-$C_{12})$ heterocycloalkyl In one embodiment, the polymerization conditions comprise heat. In some cases the polymer substrate is cured at about 80° C. for about 2 hours. Higher temperatures such as this can be used to decrease the polymerization or curing time although the monomer mixture can be polymerized at room temperature (about 25° C.) for about one day. As would be obvious to one of skill in the art, the exact polymerization conditions used can vary greatly based on the requirements for a given monomer mixture. Determination of the polymerization conditions is within the skill of one in the art.

In one embodiment, $R^1$ is hydrogen.

In one embodiment, $R^2$ is alkyl substituted with an oxo and halo group.

In one embodiment, X is nitro.

In one embodiment, $L^1$ and $L^2$ are $(C_1$-$C_{12})$alkylene.

In one embodiment, $R^1$ is hydrogen; $R^2$ is alkyl substituted with an oxo and halo group; X is nitro; and $L^1$ and $L^2$ are $(C_1$-$C_{12})$alkylene.

Also disclosed herein is a method of preparing a surface functionalized poly(dimethylsiloxane) (PDMS) substrate, comprising contacting a monomer mixture with a compound of Formula II under polymerization conditions.

II

In one embodiment, the monomer mixture comprises a poly(dimethylmethylvinylsiloxane) prepolymer. In another embodiment, the monomer mixture further comprises a poly (dimethylmethylhydrogensiloxane) precursor. In the case where the monomer mixture comprises a poly(dimethyl-methylvinylsiloxane) prepolymer and a poly(dimethylmethylhydrogensiloxane) precursor, the compound is incorporated therein at a ratio of from about 10:1:0.5 to about $10:1:10^{-3}$. In one embodiment, the ration of poly(dimethylmethylvinylsiloxane) prepolymer and poly(dimethylmethylhydrogensiloxane) precursor to the compound is about 10:1:0.5, or alternatively, about 10:1:0.1, or alternatively, about 10:1:0.05, or alternatively, about $10:1:10^{-2}$, or alternatively, or alternatively, about $10:1:10^{-3}$.

Surface Initiated Atom Transfer Radical Polymerization (SI-ATRP) to Add a Functionalized Polymer Layer Once the surface functionalized poly(dimethylsiloxane) (PDMS) is provided as disclosed herein, a functionalized polymer layer can be deposited on the surface thereof. In one embodiment, the surface functionalized poly(dimethylsiloxane) (PDMS) disclosed herein further comprises a functionalized polymer layer bonded to the compound of Formula III. This can be accomplished by contacting a functionalized monomer with the surface functionalized poly(dimethylsiloxane) (PDMS) under polymerizing conditions thus providing the functionalized polymer layer. In some embodiments, the functionalized polymer layer is the outermost layer. Various functionalized monomers can be used in the methods disclosed herein and are known to those of skill in the art. In some embodiments, the functionalized polymer layer comprises oligo(ethylene glycol).

In some embodiments, the polymerizing conditions comprise heating the monomers to about 80° C. In some embodiments, the reaction conditions comprise first forming a monomer mixture comprising a catalyst prior to contacting the surface functionalized poly(dimethylsiloxane) (PDMS). In some embodiments, the second polymerizing conditions comprise heating the monomer and linker to a temperature of from about 25° C. to about 90° C. Alternatively, in some embodiments, the second polymerizing conditions comprise allowing the monomer to react with the polymer substrate for about two days at room temperature (about 25° C.). The height of the functionalized polymer layer is largely dependent on the polymerization reaction time. In some embodiments, the polymerizing conditions comprise a deoxygenating step.

Also disclosed herein is a method for making a surface functionalized poly(dimethylsiloxane) (PDMS) having a functionalized polymer layer, said method comprising:

1) polymerizing a mixture comprising a poly(dimethylmethylvinylsiloxane) prepolymer, poly(dimethyl-methylhydrogensiloxane) precursors and a compound of Formula I to provide a surface functionalized poly(dimethylsiloxane) (PDMS):

I wherein:

$R^1$ is hydrogen or methyl;

$R^2$ is selected from the group consisting of alkyl optionally substituted with 1-3 $R^4$ groups, haloalkyl optionally substituted with 1-3 $R^4$ groups, aryl optionally substituted with 1-4 $R^4$ groups, cycloalkyl optionally substituted with 1-4 $R^4$ groups, heterocycloalkyl optionally substituted with 1-4 $R^4$ groups, and heteroaryl optionally substituted with 1-4 $R^4$ groups;

X is selected from the group consisting of nitro, $-N(R^3)_3^+$, trifluoromethyl, cyano, $-C(O)OR^3$, $-C(O)R^3$, where $R^3$ is hydrogen or alkyl; and $L^1$ and $L^2$ are independently selected from the group consisting of a direct bond, methylene optionally substituted with 1-2 $R^4$ groups, $(C_2$-$C_{12})$alkylene optionally substituted with 1-4 $R^4$ groups, $(C_6$-$C_{12})$arylene optionally substituted with 1-4 $R^4$ groups, $(C_3$-$C_{12})$cycloalkylene optionally substituted with 1-4 $R^4$ groups, $(C_3$-$C_{12})$heterocycloalkylene optionally substituted with 1-4 R⁴ groups, and (C₆-C₁₂)heteroarylene optionally substituted with 1-4 R⁴ groups; and R⁴ is selected from the group consisting of halo, nitro, cyano, oxo, aminoacyl, aminoacyloxy, carboxyl, carboxyl ester, carbonate ester, aminosulfonyl, (C₁-C₁₀)alkyl, (C₁-C₁₀)haloalkyl, (C₁-C₁₀)alkoxy, (C₆-C₁₂)aryl, (C₅-C₁₂)heteroaryl, (C₆-C₁₂)aryloxy, (C₃-C₁₂)cycloalkyl and (C₃-C₁₂)heterocycloalkyl; and 2) contacting a functionalized monomer with the surface functionalized poly(dimethylsiloxane) (PDMS) under polymerization conditions to provide the surface functionalized poly(dimethylsiloxane) (PDMS) having a functionalized polymer layer.

Figure 2:
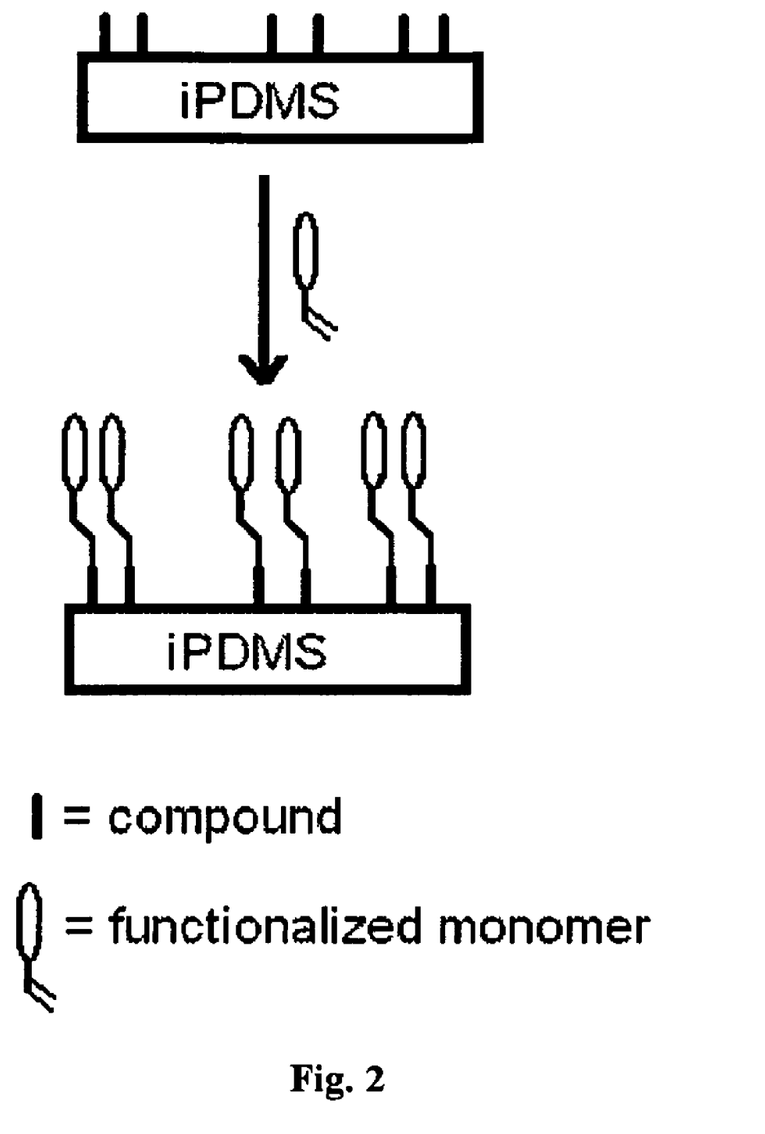
FIG. 2 is a schematic of an illustrative embodiment of the formation of a functionalized polymer on the surface of the surface functionalized PDMS using a functionalized monomer.

In some embodiments, the functionalized monomer comprises a terminal alkenyl group and a functional group. This embodiment in depicted in FIG. 2. In principal, the terminal functional group can be any functional group provided that it does not react with the compound of Formula I. In some embodiments, the terminal functional group is selected from the group consisting of a hydroxyl, amino, thio, carboxyl, carboxyl ester, amino, alpha-haloester and haloalkyl. In one embodiment, the terminal functional group is a hydroxyl. In one embodiment, the functionalized monomer is oligo(ethylene glycol) methacrylate.

In some embodiments, the polymerization conditions can result in various polymerization mechanisms. Various types of polymerizations can be used such as, for example, cationic, anionic, free radical and living polymerizations. Such polymerizations can be metal catalyzed polymerization reactions. In some embodiments, the polymerization conditions comprise a metal catalyst. Various metals can be used as a catalyst herein, such as, platinum, copper, iron, manganese, cobalt, molybdenum, tin, zinc, ruthenium, rhodium, and the like. In some embodiments, the metal comprises copper.

Further embodiments of the present disclosure can be found in PCT application No. PCT/CN2008/071944, filed Aug. 11, 2008 and entitled "Superhydrophobic Poly(dimethylsiloxane) and Methods for Making the Same", which is herein incorporated by reference in its entirety.

Methods for Using the Surface Functionalized Poly(dimethylsiloxane) (PDMS)

In some embodiments, the surface functionalized poly(dimethylsiloxane) (PDMS) further comprises at least one indentation on the surface. This can be accomplished using a number of known methods, such as photolithography, soft lithography, isotropic or anisotropic etching, or with the use of a mold. Such technologies are well known in the art (Xia, et al., *Angew Chem. Int. Ed*, 1998, 37, 550-575). For example, the formation of channels on the surface of the functionalized via photolithography is depicted in FIG. 1.

It is contemplated that the surface functionalized poly(dimethylsiloxane) (PDMS) can be produced in any theoretical size or shape so long as the bulk properties of the poly(dimethylsiloxane) (PDMS) are not effected. In some embodiments, the surface functionalized poly(dimethylsiloxane) (PDMS) is a microfluidic device.

Also disclosed herein is a method for producing a microfluidic device, comprising:

1) providing a poly(dimethylsiloxane) (PDMS) polymer substrate having a compound of Formula III incorporated therein:

III wherein:

R¹ is hydrogen or methyl;

R² is selected from the group consisting of alkyl optionally substituted with 1-3 R⁴ groups, haloalkyl optionally substituted with 1-3 R⁴ groups, aryl optionally substituted with 1-4 R⁴ groups, cycloalkyl optionally substituted with 1-4 R⁴ groups, heterocycloalkyl optionally substituted with 1-4 R⁴ groups, and heteroaryl optionally substituted with 1-4 R⁴ groups;

X is selected from the group consisting of nitro, —N(R³)₃⁺, trifluoromethyl, cyano, —C(O)OR³, —C(O)R³, where R³ is hydrogen or alkyl; and L¹ and L² are independently selected from the group consisting of a direct bond, methylene optionally substituted with 1-2 R⁴ groups, (C₂-C₁₂)alkylene optionally substituted with 1-4 R⁴ groups, (C₆-C₁₂)arylene optionally substituted with 1-4 R⁴ groups, (C₃-C₁₂)cycloalkylene optionally substituted with 1-4 R⁴ groups, (C₃-C₁₂)heterocycloalkylene optionally substituted with 1-4 R⁴ groups, and (C₆-C₁₂)heteroarylene optionally substituted with 1-4 R⁴ groups; and R⁴ is selected from the group consisting of halo, nitro, cyano, oxo, aminoacyl, aminoacyloxy, carboxyl, carboxyl ester, carbonate ester, aminosulfonyl, (C₁-C₁₀)haloalkyl, (C₁-C₁₀)alkoxy, (C₆-C₁₂)aryl, (C₅-C₁₂)heteroaryl, (C₆-C₁₂)aryloxy, (C₃-C₁₂)cycloalkyl and (C₃-C₁₂)heterocycloalkyl; and 2) applying a photomask to a surface of the functionalized poly(dimethylsiloxane) (PDMS) substrate; and 3) irradiating at a wavelength of from about 150 nm to about 400 nm, to produce the microfluidic device.

In some embodiments, R¹ is hydrogen.

In some embodiments, wherein R² is alkyl substituted with an oxo and halo group.

In some embodiments, X is nitro.

In some embodiments, L¹ and L² are (C₁-C₁₂)alkylene.

In some embodiments, R¹ is hydrogen; R² is alkyl substituted with an oxo and halo group; X is nitro; and L¹ and L² are (C₁-C₁₂)alkylene.

Also disclosed herein is a method for producing a microfluidic device, comprising:

1) providing a poly(dimethylsiloxane) (PDMS) polymer substrate having a compound of Formula II incorporated therein:

2) applying a photomask to a surface of the functionalized poly(dimethylsiloxane) (PDMS) substrate; and 3) irradiating at a wavelength of from about 150 nm to about 400 nm, to provide the microfluidic device.

In some embodiments, the method further comprises the addition of a functionalized polymer layer bonded to the compound of Formula III. In one embodiment, the functionalized polymer layer comprises oligo(ethylene glycol).

It is contemplated that the surface functionalized poly (dimethylsiloxane) (PDMS) disclosed herein can be used in all of the applications where standard PDMS is used. For example, for the fabrication of microfluidic devices, bioMEMS, microelectronics, biotechnology, microreactors, microsensors, microanalyzers, microoptics, and in research.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

EXAMPLES

The present technology is further illustrated by the following examples, which should not be construed as limiting in any way. All numerical designations, e.g., pH, temperature, time, concentration, and molecular weight, including ranges, are approximations which are varied (+) or (−) by increments of 10%. It is to be understood, although not always explicitly stated that all numerical designations are preceded by the term "about". It also is to be understood, although not always explicitly stated, that the reagents described herein are merely exemplary and that equivalents of such are known in the art.

These and other embodiments of the present technology will readily occur to those of ordinary skill in the art in view of the disclosure herein and are specifically contemplated.

The present technology is further understood by reference to the following examples, which are intended to be purely exemplary of the present technology. The present technology is not limited in scope by the exemplified embodiments, which are intended as illustrations of single aspects of the present technology only. Any methods that are functionally equivalent are within the scope of the present technology. Various modifications of the present technology in addition to those described herein will become apparent to those skilled in the art from the foregoing description and accompanying figures. Such modifications fall within the scope of the appended claims.

Example 1

Synthesis of Compound II

Compound 2 (38.8 mmol) was added into a flask containing compound 1 (40.0 mmol), dry tetrahydrofuran (40 mL), and 4-dimethylaminopyridine (DMAP, 47.7 mmol) in a dropwise fashion. The mixture was stirred at room temperature for 5 h, diluted with tetrahydrofuran, and filtered. A 2N HCl aqueous solution was used to neutralize the filtrate and ethyl ether was used to extract the organic phase four times. The organic extracts were combined and dried over anhydrous sodium sulfate. After the removal of solvents by a rotavapor, the crude product was purified by column chromatography ($CH_2Cl_2$/hexanes, 1:1, v/v) to give compound 3 (84.0%).

To a flask with dry tetrahydrofuran (40 mL) under $N_2$ atmosphere, compound 3 (1.9 mmol) and compound 4 (1.9 mmol) were mixed along with NaOH and hexamethylphosphoramide (HMPA). The mixture was stirred at room temperature overnight, diluted with tetrahydrofuran, and filtered. A 2N HCl aqueous solution was used to neutralize the filtrate and ethyl ether was used to extract the organic phase four times. The organic extracts were combined and dried over anhydrous sodium sulfate. After the removal of solvents by a rotavapor, the crude product was purified by column chromatography (CH$_2$Cl$_2$/hexanes, 10:1, v/v) to give compound II (54.0%). Putative $^{13}$C-NMR calculated using ChemDraw Ultra® version 10.0, in ppm relative to TMS: δ 211.3, 173.1, 165.9, 147.3, 139.1, 138.5, 136.2, 128.4, 127.9, 123.7, 115.7, 64.8, 63.6, 58.9, 36.0, 33.9, 33.9, 32.1, 32.1, 31.7, 29.7, 29.7, 29.6, 29.3, 29.3, 29.3, 29.1, 29.0, 25.8, 25.0, 23.1.

Example 2

Preparation of a Surface Functionalized Poly(dimethylsiloxane) (PDMS)

Figure 3:
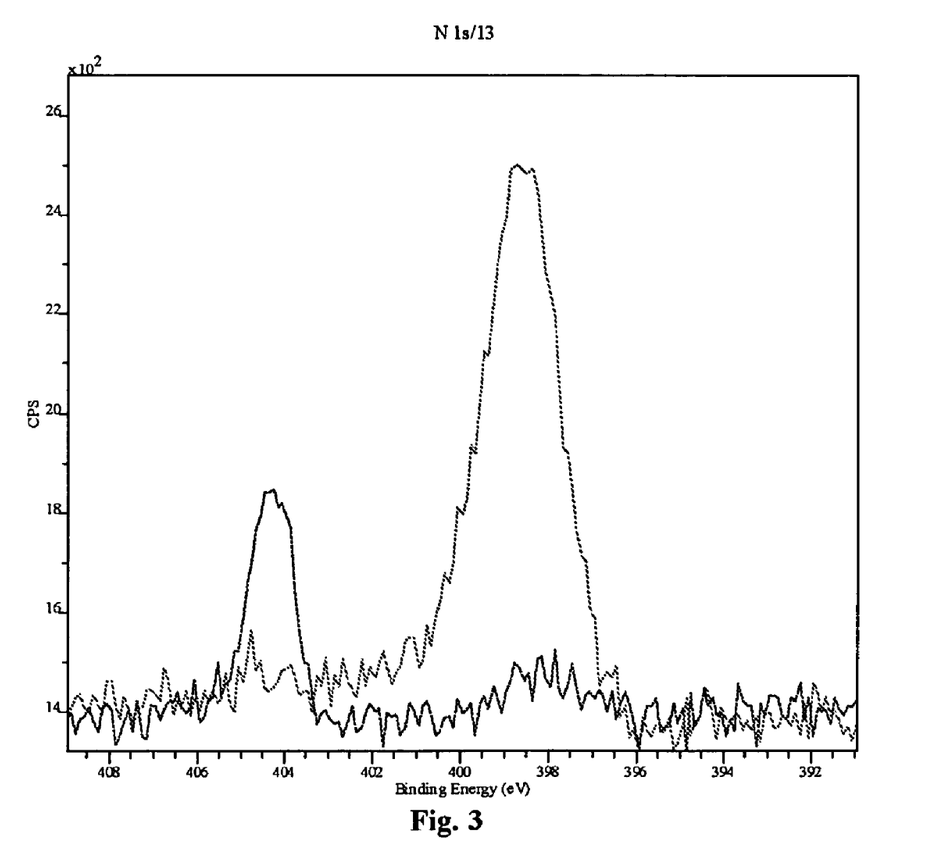
FIG. 3 shows the shift in the nitrogen signal from before (the peak on the left) and after (the peak on the right) exposure to UV irradiation confirming the decomposition of compound II.

According to the method shown in FIG. 1, prepolymer A (polydimethyl-methylvinylsiloxane), cross-linker B (vinyl-endcapped polydimethyl-methylvinylsiloxane) and compound II (from example 1) were mixed at a ratio of 10:1:0.2 and cured at 80° C. to form the surface functionalized poly (dimethylsiloxane) (PDMS). X-ray photoelectron spectroscopy (XPS) was applied to characterize the surface composition of the PDMS. FIG. 3 shows the shift in the nitrogen signal from before (the peak on the left) and after (the peak on the right) exposure to UV irradiation confirming the decomposition of compound II. Compared with regular PDMS, compound II referred (a unique Br 3d peak at 71 eV) were presented at the surface of the PDMS and accomplished the surface modification of PDMS.

The surface functionalized poly(dimethylsiloxane) was then exposed to UV light (360-370 nm) through a photomask (see FIG. 1) to form surface patterns of compound II.

Example 3

1. Surface Initiated Atom Transfer Radical Polymerization (SI-ATRP) to Add a Functionalized Polymer Layer Surface initiated atom transfer radical polymerization (SI-ATRP) of oligo(ethylene glycol) methacrylate was performed on the surface functionalized poly(dimethylsiloxane) for permanent and functional surface coating. The surface functionalized poly(dimethylsiloxane) was placed in a 100 ml bottle and processed anaerobic treatment. The functionalized polymer layer was obtained by mixing well with water (5 mL), methanol (10 mL), and the monomer oligo(ethylene glycol) methacrylate (8 mmol, 0.35 M), CuBr (36 mg, 0.25 mmol) and bipyridine (78 mg, 0.5 mmol) resulting in a dark-red solution. The solution was deoxygenated just before use. The mixture was transferred into the bottle with the surface functionalized poly(dimethylsiloxane) under inert gas protection. The reaction was continued for 24 hours at 20° C. The surface functionalized poly(dimethylsiloxane) was rinsed with methanol and Milli-Q® water, and dried under flowing nitrogen. XPS characterization confirmed the success of polymerization and film deposition on the surface of the surface functionalized poly(dimethylsiloxane).

2. Equivalents

The present disclosure is not to be limited in terms of the particular embodiments described in this application, which are intended as single illustrations of individual aspects of. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A compound of Formula I:

wherein:
R$^1$ is hydrogen or methyl;
R$^2$ is alkyl substituted with an oxo and halo group;
X is selected from the group consisting of nitro, —N(R$^3$)$_3^+$, trifluoromethyl, cyano, —C(O)OR$^3$, —C(O)R$^3$, where R$^3$ is hydrogen or alkyl; and
L$^1$ and L$^2$ are independently selected from the group consisting of a direct bond, methylene optionally substituted with 1-2 R$^4$ groups, (C$_2$-C$_{12}$)alkylene optionally substituted with 1-4 R$^4$ groups, (C$_6$-C$_{12}$)arylene optionally substituted with 1-4 R$^4$ groups, (C$_3$-C$_{12}$)cycloalkylene optionally substituted with 1-4 R$^4$ groups, (C$_3$-C$_{12}$) heterocycloalkylene optionally substituted with 1-4 R$^4$ groups, and (C$_6$-C$_{12}$)heteroarylene optionally substituted with 1-4 R$^4$ groups; and R$^4$ is selected from the group consisting of halo, nitro, cyano, oxo, aminoacyl, aminoacyloxy, carboxyl, carboxyl ester, carbonate ester, aminosulfonyl, (C$_1$-C$_{10}$) alkyl, (C$_1$-C$_{10}$)haloalkyl, (C$_1$-C$_{10}$)alkoxy, (C$_6$-C$_{12}$)aryl, (C$_5$-C$_{12}$)heteroaryl, (C$_6$-C$_{12}$)aryloxy, (C$_3$-C$_{12}$)cycloalkyl and (C$_3$-C$_{12}$)heterocycloalkyl.

2. The compound of claim 1, wherein R$^1$ is hydrogen.
3. The compound of claim 1, wherein X is nitro.
4. The compound of claim 1, wherein L$^1$ and L$^2$ are (C$_1$-C$_{12}$)alkylene.
5. The compound of claim 1, wherein R$^1$ is hydrogen; X is nitro; and L$^1$ and L$^2$ are (C$_1$-C$_{12}$)alkylene.
6. A surface functionalized poly(dimethylsiloxane) (PDMS), comprising a polydimethyl siloxane (PDMS) substrate having a compound of Formula III incorporated therein:

wherein:
R$^1$ is hydrogen or methyl;
R$^2$ is selected from the group consisting of alkyl optionally substituted with 1-3 R$^4$ groups, haloalkyl optionally substituted with 1-3 R$^4$ groups, aryl optionally substituted with 1-4 R$^4$ groups, cycloalkyl optionally substituted with 1-4 R$^4$ groups, heterocycloalkyl optionally substituted with 1-4 R$^4$ groups, and heteroaryl optionally substituted with 1-4 R$^4$ groups;
X is selected from the group consisting of nitro, —N(R$^3$)$_3^+$, trifluoromethyl, cyano, —C(O)OR$^3$, —C(O)R$^3$, where R$^3$ is hydrogen or alkyl; and
L$^1$ and L$^2$ are independently selected from the group consisting of a direct bond, methylene optionally substituted with 1-2 R$^4$ groups, (C$_2$-C$_{12}$)alkylene optionally substituted with 1-4 R$^4$ groups, (C$_6$-C$_{12}$)arylene optionally substituted with 1-4 R$^4$ groups, (C$_3$-C$_{12}$)cycloalkylene optionally substituted with 1-4 R$^4$ groups, (C$_3$-C$_{12}$) heterocycloalkylene optionally substituted with 1-4 R$^4$ groups, and (C$_6$-C$_{12}$)heteroarylene optionally substituted with 1-4 R$^4$ groups; and
R$^4$ is selected from the group consisting of halo, nitro, cyano, oxo, aminoacyl, aminoacyloxy, carboxyl, carboxyl ester, carbonate ester, aminosulfonyl, (C$_1$-C$_{10}$) alkyl, (C$_1$-C$_{10}$)haloalkyl, (C$_1$-C$_{10}$)alkoxy, (C$_6$-C$_{12}$)aryl, (C$_5$-C$_{12}$)heteroaryl, (C$_6$-C$_{12}$)aryloxy, (C$_3$-C$_{12}$)cycloalkyl and (C$_3$-C$_{12}$)heterocycloalkyl.

7. The surface functionalized poly(dimethylsiloxane) (PDMS) of claim 6, wherein R$^1$ is hydrogen.
8. The surface functionalized poly(dimethylsiloxane) (PDMS) of claim 6, wherein R$^2$ is alkyl substituted with an oxo and halo group.

9. The surface functionalized poly(dimethylsiloxane) (PDMS) of claim 6, wherein X is nitro.

10. The surface functionalized poly(dimethylsiloxane) (PDMS) of claim 6, wherein $L^1$ and $L^2$ are $(C_1-C_{12})$alkylene.

11. The surface functionalized poly(dimethylsiloxane) (PDMS) of claim 6, wherein $R^1$ is hydrogen; $R^2$ is alkyl substituted with an oxo and halo group; X is nitro; and $L^1$ and $L^2$ are $(C_1-C_{12})$alkylene.

12. The surface functionalized poly(dimethylsiloxane) (PDMS) of claim 6, wherein the compound is incorporated therein at a ratio of from about 11:0.5 to about $11:10^{-3}$.

13. The surface functionalized poly(dimethylsiloxane) (PDMS) of claim 6, further comprising a functionalized polymer layer bonded to the compound of Formula III.

14. The surface functionalized poly(dimethylsiloxane) (PDMS) of claim 13, wherein the functionalized polymer layer comprises oligo(ethylene glycol).

15. The surface functionalized poly(dimethylsiloxane) (PDMS) of claim 6, having a contact angle of from about 90 to about 120 degrees.

16. The surface functionalized poly(dimethylsiloxane) (PDMS) of claim 6, having a contact angle of about 114 degrees.

17. A method of preparing a surface functionalized poly (dimethylsiloxane) (PDMS) substrate, comprising contacting a monomer mixture with a compound of Formula I under polymerization conditions:

wherein:
$R^1$ is hydrogen or methyl;
$R^2$ is selected from the group consisting of alkyl optionally substituted with 1-3 $R^4$ groups, haloalkyl optionally substituted with 1-3 $R^4$ groups, aryl optionally substituted with 1-4 $R^4$ groups, cycloalkyl optionally substituted with 1-4 $R^4$ groups, heterocycloalkyl optionally substituted with 1-4 $R^4$ groups, and heteroaryl optionally substituted with 1-4 $R^4$ groups;

X is selected from the group consisting of nitro, $-N(R^3)_3^+$, trifluoromethyl, cyano, $-C(O)OR^3$, $-C(O)R^3$, where $R^3$ is hydrogen or alkyl; and $L^1$ and $L^2$ are independently selected from the group consisting of a direct bond, methylene optionally substituted with 1-2 $R^4$ groups, $(C_2-C_{12})$alkylene optionally substituted with 1-4 $R^4$ groups, $(C_6-C_{12})$arylene optionally substituted with 1-4 $R^4$ groups, $(C_3-C_{12})$cycloalkylene optionally substituted with 1-4 $R^4$ groups, $(C_3-C_{12})$heterocycloalkylene optionally substituted with 1-4 $R^4$ groups, and $(C_6-C_{12})$heteroarylene optionally substituted with 1-4 $R^4$ groups; and $R^4$ is selected from the group consisting of halo, nitro, cyano, oxo, aminoacyl, aminoacyloxy, carboxyl, carboxyl ester, carbonate ester, aminosulfonyl, $(C_1-C_{10})$alkyl, $(C_1-C_{10})$haloalkyl, $(C_1-C_{10})$alkoxy, $(C_6-C_{12})$aryl, $(C_5-C_{12})$heteroaryl, $(C_6-C_{12})$aryloxy, $(C_3-C_{12})$cycloalkyl and $(C_3-C_{12})$heterocycloalkyl;

to provide a functionalized poly(dimethylsiloxane) (PDMS) substrate.

18. The method of claim 17, wherein the compound is of Formula II:

19. The method of claim 18, wherein the monomer mixture comprises a poly(dimethylmethylvinylsiloxane) prepolymer.

* * * * *

UNITED STATES PATENT AND TRADEMARK OFFICE
CERTIFICATE OF CORRECTION

| | | |
|---|---|---|
| PATENT NO. | : 8,022,157 B2 | Page 1 of 1 |
| APPLICATION NO. | : 12/529229 | |
| DATED | : September 20, 2011 | |
| INVENTOR(S) | : Ma | |

It is certified that error appears in the above-identified patent and that said Letters Patent is hereby corrected as shown below:

On the Title Page, Item (56), under "OTHER PUBLICATIONS", Line 14, delete "Chem.Soc.," and insert -- Chem. Soc., --, therefor.

In Column 8, Line 19, delete "Ed," and insert -- Ed., --, therefor.

In Column 15, Line 4, delete "heterocycloalkyl" and insert -- heterocycloalkyl. --, therefor.

In Column 16, Line 30, delete "Ito" and insert -- I to --, therefor.

In Column 17, Line 23, delete "amino," and insert -- amido, --, therefor.

In Column 17, Line 52, delete "Ed," and insert -- Ed., --, therefor.

Signed and Sealed this
Seventeenth Day of April, 2012

David J. Kappos
*Director of the United States Patent and Trademark Office*